(12) United States Patent
Heimbrock et al.

(10) Patent No.: US 9,333,134 B2
(45) Date of Patent: *May 10, 2016

(54) MEDICAL GAS TANK RECEPTACLE FOR PATIENT SUPPORT APPARATUS

(71) Applicant: Hill-Rom Services, Inc., Batesville, IN (US)

(72) Inventors: Richard H. Heimbrock, Cincinnati, OH (US); Jonathan D. Turner, Dillsboro, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 58 days.

This patent is subject to a terminal disclaimer.

(21) Appl. No.: 14/269,492

(22) Filed: May 5, 2014

(65) Prior Publication Data

US 2014/0237720 A1    Aug. 28, 2014

Related U.S. Application Data

(63) Continuation of application No. 13/733,962, filed on Jan. 4, 2013, now Pat. No. 8,713,728, which is a continuation of application No. PCT/US2011/043392, filed on Jul. 8, 2011.

(60) Provisional application No. 61/369,152, filed on Jul. 30, 2010, provisional application No. 61/369,499, filed on Jul. 30, 2010.

(51) Int. Cl.
| | |
|---|---|
| A47C 21/00 | (2006.01) |
| A61G 7/05 | (2006.01) |
| B65D 25/00 | (2006.01) |
| F17C 13/08 | (2006.01) |
| A61M 16/10 | (2006.01) |

(52) U.S. Cl.
CPC ............. *A61G 7/0503* (2013.01); *B65D 25/00* (2013.01); *F17C 13/085* (2013.01); *A61G 2203/723* (2013.01); *A61M 16/10* (2013.01); *A61M 2202/0208* (2013.01); *A61M 2209/082* (2013.01); *F17C 2201/058* (2013.01); *F17C 2205/0111* (2013.01); *F17C 2205/0126* (2013.01); *F17C 2221/011* (2013.01); *F17C 2270/025* (2013.01); *F17C 2270/0745* (2013.01)

(58) Field of Classification Search
CPC ..... A61G 12/002; A61G 5/10; A61G 12/008; A61G 7/05; A61G 7/0503; A61G 2203/723; F17C 13/085; B65D 25/00; A61M 2202/0208; A61M 2209/082; A61M 16/10
See application file for complete search history.

(56) References Cited

U.S. PATENT DOCUMENTS

| | | | | |
|---|---|---|---|---|
| 1,064,248 | A | * 6/1913 | Pohle | B65D 1/0276 |
| | | | | 220/485 |
| 1,906,590 | A | * 5/1933 | Hewson | B60B 33/00 |
| | | | | 16/18 CG |
| 3,970,344 | A | 7/1976 | Baumann | |
| 4,026,435 | A | * 5/1977 | Hendon | A47J 36/022 |
| | | | | 206/549 |

(Continued)

*Primary Examiner* — Robert G Santos
*Assistant Examiner* — Myles Throop
(74) *Attorney, Agent, or Firm* — Barnes & Thornburg LLP

(57) ABSTRACT

A fluid tank receptacle comprises a housing, a cage, and a retainer. The housing includes an opening therethrough configured to receive a fluid tank. The cage movably engages the housing and configured to support the fluid tank. The retainer is coupled to the housing and is configured to movably retain a portion of the cage within the housing such that the cage is able to move between a storage position and a use position with respect to the housing.

16 Claims, 11 Drawing Sheets

(56) References Cited

U.S. PATENT DOCUMENTS

| | | | |
|---|---|---|---|
| 4,213,648 A | 7/1980 | Steichen | |
| 4,431,206 A | 2/1984 | Pryor | |
| 4,506,903 A * | 3/1985 | Bowermaster | A61G 5/10 280/304.1 |
| 4,696,420 A | 9/1987 | Kulik | |
| D305,629 S | 1/1990 | Wood | |
| D342,222 S | 12/1993 | Cherry | |
| 5,283,919 A | 2/1994 | Grant | |
| 5,288,001 A | 2/1994 | Locarno | |
| D357,217 S | 4/1995 | Shirley | |
| 5,556,065 A | 9/1996 | Wadley | |
| 5,715,548 A | 2/1998 | Weismiller et al. | |
| 5,788,475 A * | 8/1998 | Henderson | B63C 11/30 405/185 |
| 5,890,687 A | 4/1999 | Pryor et al. | |
| 5,966,760 A | 10/1999 | Gallant et al. | |
| 5,996,150 A | 12/1999 | Blevins et al. | |
| 6,163,903 A | 12/2000 | Weismiller et al. | |
| 6,170,518 B1 * | 1/2001 | Ratelle | F17C 13/084 137/343 |
| 6,325,097 B1 * | 12/2001 | Gallant | A61G 12/001 137/505 |
| 6,336,235 B1 | 1/2002 | Ruehl | |
| 6,360,389 B1 | 3/2002 | Gallant et al. | |
| 6,427,270 B1 | 8/2002 | Blevins et al. | |
| 6,585,206 B2 | 7/2003 | Metz et al. | |
| 6,672,321 B2 | 1/2004 | Hamilton | |
| 6,691,349 B2 | 2/2004 | Blevins | |
| 6,966,086 B2 | 11/2005 | Metz et al. | |
| 7,017,208 B2 | 3/2006 | Weismiller et al. | |
| D528,904 S | 9/2006 | Reding | |
| 7,124,456 B2 | 10/2006 | Palmatier et al. | |
| 7,188,855 B1 | 3/2007 | Thomas | |
| 7,213,279 B2 | 5/2007 | Weismiller et al. | |
| 7,237,287 B2 | 7/2007 | Weismiller et al. | |
| 7,243,666 B2 | 7/2007 | Carroll | |
| 7,338,055 B2 | 3/2008 | Fuentes | |
| 7,370,660 B2 | 5/2008 | Hamilton et al. | |
| 7,395,564 B2 | 7/2008 | McDaniel et al. | |
| 7,412,735 B2 | 8/2008 | McDaniel et al. | |
| 7,480,951 B2 | 1/2009 | Weismiller et al. | |
| 7,568,246 B2 | 8/2009 | Weismiller et al. | |
| 7,624,463 B2 * | 12/2009 | Graham | A61G 7/0503 5/600 |
| 7,648,113 B2 | 1/2010 | Johnson | |
| D618,356 S | 6/2010 | Ross | |
| 7,731,136 B1 | 6/2010 | Chisolm et al. | |
| 7,784,128 B2 | 8/2010 | Kramer | |
| 7,844,735 B2 | 11/2010 | Andreev et al. | |
| 7,913,337 B1 | 3/2011 | Masson | |
| 8,011,634 B1 | 9/2011 | Johnson | |
| 8,065,764 B2 | 11/2011 | Kramer | |
| 8,240,684 B2 | 8/2012 | Ross et al. | |
| 8,413,274 B2 | 4/2013 | Weismiller et al. | |
| 2002/0074755 A1 * | 6/2002 | Burkett | B62B 1/125 280/47.26 |
| 2006/0021144 A1 * | 2/2006 | Hornbach | A61G 7/002 5/618 |
| 2007/0018058 A1 * | 1/2007 | Graham | A61G 7/0503 248/125.7 |
| 2008/0189858 A1 * | 8/2008 | Merritt | A61G 1/04 5/503.1 |
| 2008/0263769 A1 * | 10/2008 | Newkirk | A61G 7/05 5/503.1 |
| 2010/0077549 A1 * | 4/2010 | Hensley | G06K 7/0008 5/618 |
| 2011/0010861 A1 * | 1/2011 | Heimbrock | A61G 7/015 5/618 |
| 2012/0110741 A1 * | 5/2012 | Mears | A61G 7/0506 5/618 |
| 2013/0145551 A1 | 6/2013 | Heimbrock et al. | |
| 2014/0097313 A1 * | 4/2014 | Hesketh | A61G 7/0503 248/226.11 |

* cited by examiner

MEDICAL GAS TANK RECEPTACLE FOR PATIENT SUPPORT APPARATUS

CROSS-REFERENCE TO RELATED APPLICATIONS

This application is a continuation of U.S. application Ser. No. 13/733,962, filed Jan. 4, 2013, now U.S. Pat. No. 8,713,728, which is a continuation of PCT International Application No. PCT/US2011/043392 which was filed Jul. 8, 2011, which is hereby expressly incorporated by reference herein, and which claimed the benefit of U.S. Provisional Patent Application No. 61/369,152 filed Jul. 30, 2010 and U.S. Provisional Patent Application No. 61/369,499 filed Jul. 30, 2010, each of which is hereby expressly incorporated by reference herein. PCT International Application No. PCT/US2011/043392 also claimed priority to U.S. application Ser. No. 12/847,337 filed Jul. 30, 2010; U.S. application Ser. No. 12/833,321 filed Jul. 9, 2010; and U.S. application Ser. No. 12/836,606 filed Jul. 15, 2010; but the present application does not claim priority to any of those three U.S. utility patent applications.

BACKGROUND

This disclosure relates generally to person-support apparatuses. More particularly, but not exclusively, one illustrative embodiment relates to a person-support apparatus with a fluid tank receptacle.

Person-support apparatuses in hospitals can often have fluid tanks coupled thereto that can be used to supply fluid to a person supported on the person-support apparatus. While various devices have been developed, there is still room for development. Thus a need persists for further contributions in this area of technology.

SUMMARY

The present disclosure includes one or more of the features recited in the appended claims and/or the following features which, alone or in any combination, may comprise patentable subject matter.

One illustrative embodiment of the present disclosure can include fluid tank receptacle with a cage configured to extend from the upper frame a first distance to support a fluid tank when it is positioned in the fluid tank receptacle and retract toward the upper frame such that the cage is a second distance from the upper frame that can be less than the first distance when the fluid tank is not positioned in the fluid tank receptacle. Another illustrative embodiment of the present disclosure can include an upper frame with an upper frame base supporting a deck with a seat section having stationary side portions coupled to the upper frame base and movable middle portions positioned between the stationary side portions that can be configured to cooperate with a head deck section and a foot deck section to move the upper frame between a substantially horizontal position and a chair position.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION

Figure 1:
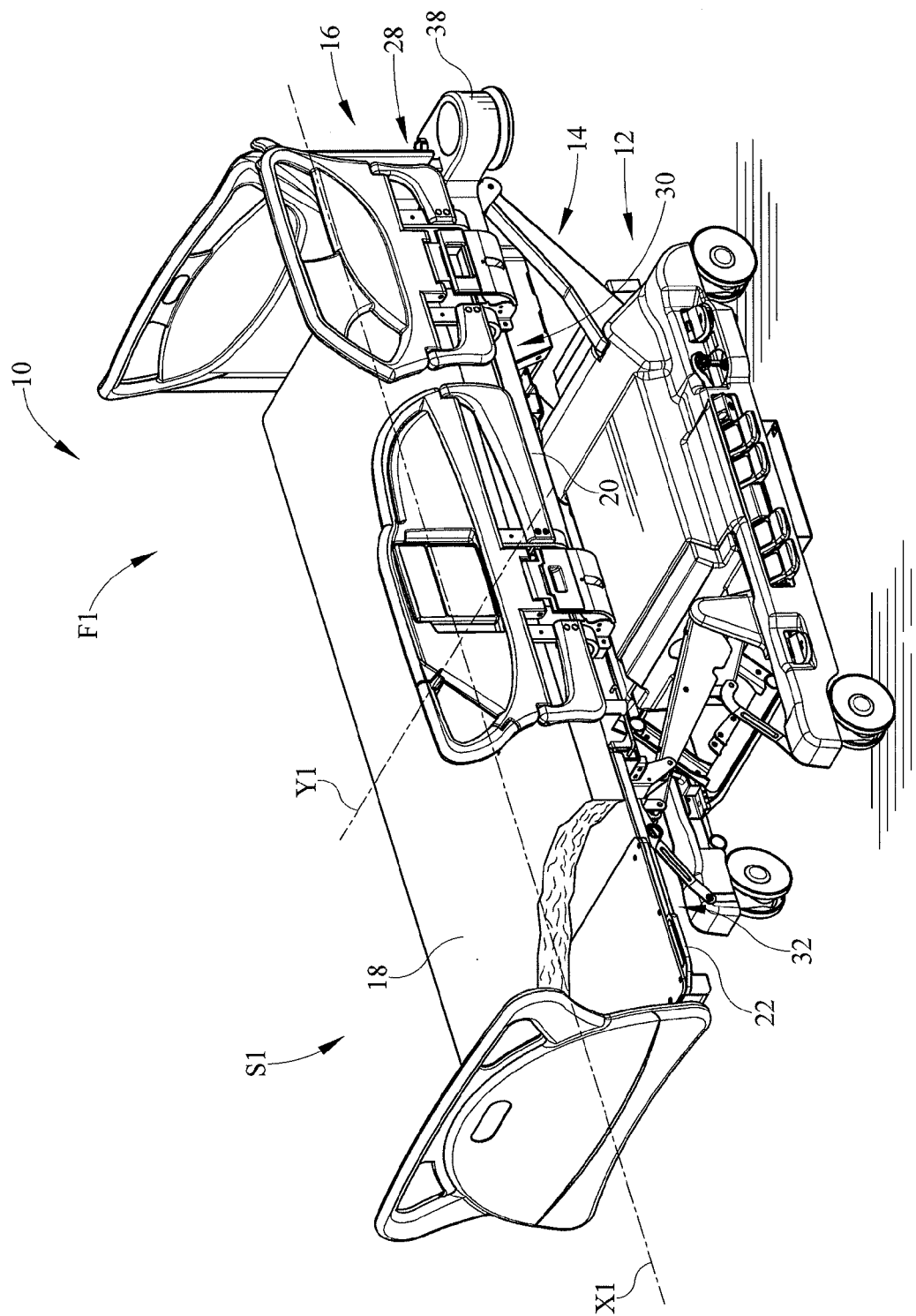
FIG. 1 is a perspective side view of a person-support apparatus according to one illustrative embodiment with the upper frame in a substantially horizontal orientation and including a fluid tank receptacle.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment of the present disclosure can include fluid tank storage assembly with cage configured to extend from the upper frame a first distance when a fluid tank is stored in the fluid tank storage assembly and retract toward the upper frame such that the cage is a second distance from the upper frame that can be less than the first distance when the fluid tank is not stored in the fluid tank storage assembly. Another illustrative embodiment of the present disclosure can include an upper frame with an upper frame base supporting a deck with a seat section having stationary side portions coupled to the upper frame base and movable middle portions positioned between the stationary side portions that can be configured to cooperate with a head deck section and a foot deck section to move the upper frame between a substantially horizontal position and a chair position.

A person-support apparatus 10 according to one illustrative embodiment of the current disclosure is shown in FIGS. 1-11. The person-support apparatus 10 can be a hospital bed with a first section F1 or head support section F1, where the head of a person (not shown) can be positioned and a second section S1 or a foot support section S1, where the feet of the person (not shown) can be positioned. It should be appreciated that the person-support apparatus 10 can also be a hospital stretcher or an operating table. The person-support apparatus 10 can define a first longitudinal axis X1 passing through the first section F1 and the second section S1 and a transverse axis Y1 substantially perpendicular to the first longitudinal axis. It should be appreciated that the first longitudinal axis X1 and the transverse axis Y1 can be in the same horizontal plane. The person-support apparatus 10 can include a lower frame 12 or base 12, a plurality of supports 14 coupled with the lower frame 12 and an upper frame 16 movably supported by the plurality of supports 14 above the lower frame 12. It should be appreciated that the supports 14 can be lift mechanisms that can move the upper frame 16 with respect to the lower frame 12. It should also be appreciated that in one illustrative embodiment, the person-support apparatus 10 can support a person-support surface 18 on the upper frame 16.

Figure 2:
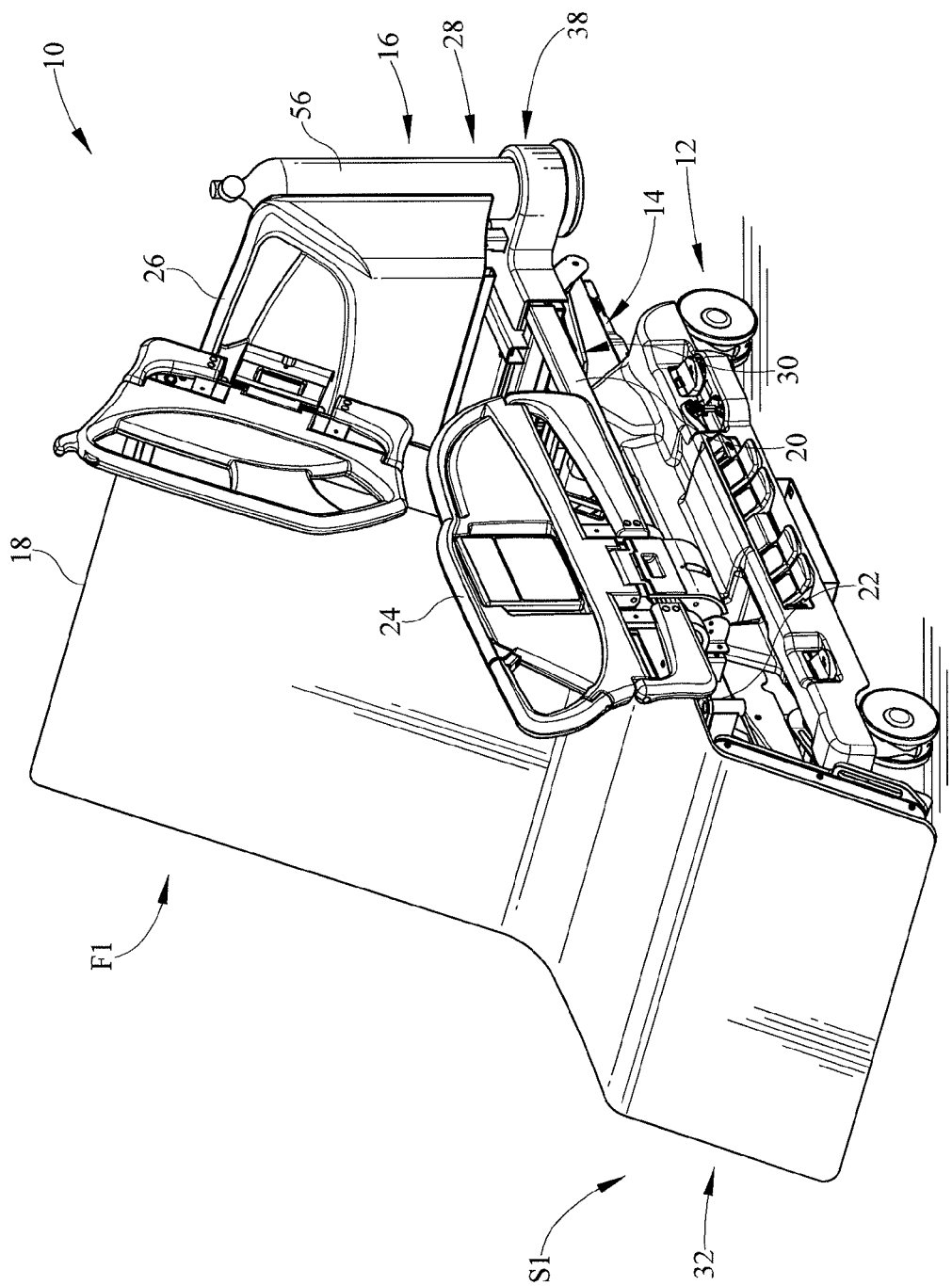
FIG. 2 is a perspective side view of a person-support apparatus according to one illustrative embodiment with the upper frame in a chair position.
Figure 10:
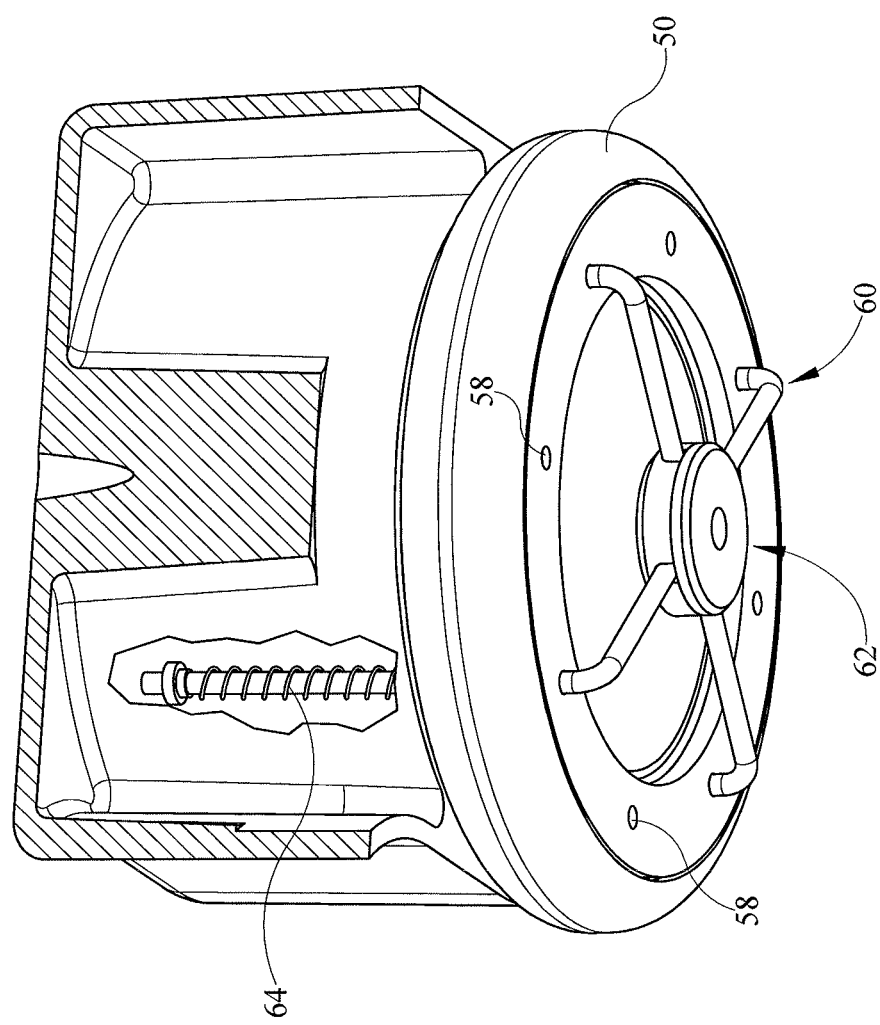
FIG. 10 is a partial cross-sectional view of the fluid tank receptacle of FIG. 1 showing the spring located in the slots in the housing at a first length when the cage is in a storage position.
Figure 11:
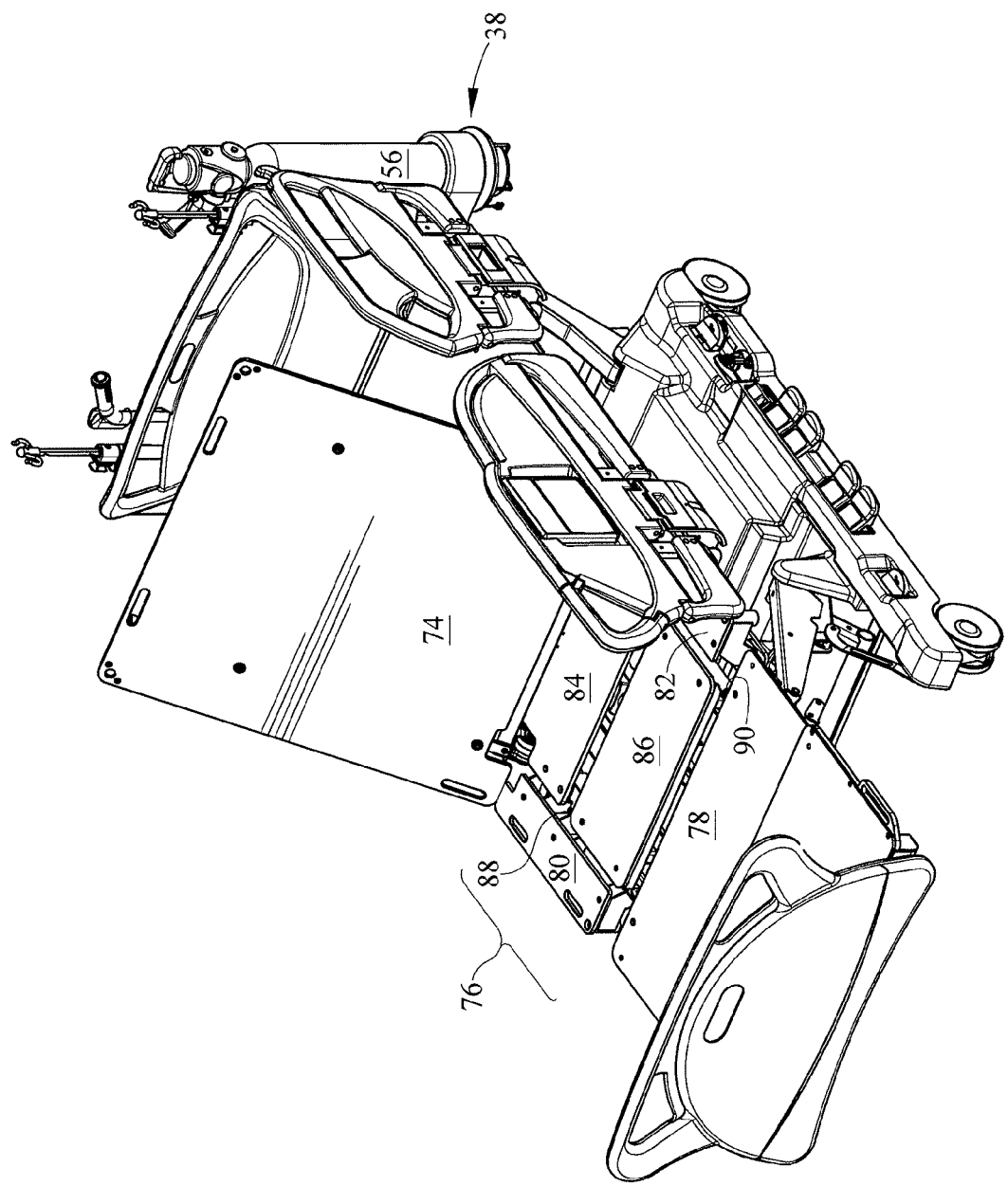
FIG. 11 is a perspective view of the patient-support apparatus of FIG. 1 showing a first movable portion in a raised orientation with respect to the upper frame.

The upper frame 16 can include an upper frame base 20, a deck 22, siderails 24, endboards 26, and an accessory support 28 as shown in FIGS. 1-2 and 11. The upper frame base 20 can be coupled with the supports 14 and can support the deck 22 thereon as shown in FIGS. 1 and 2. The accessory support 28 can be located at a head end 30 of the upper frame 16. It should be appreciated that the accessory support 28 can be located at a foot end 32 of the upper frame 16. The accessory support 28 can include transport handles 34, accessory pole receptacles 36, and fluid tank receptacles 38 as shown in FIGS. 1-11. It should be appreciated that accessory poles 40, such as, for example, IV poles and/or line management devices, can be secured to the accessory support 28. The transport handles 34 can be configured to be gripped by a person and pushed to move the person-support apparatus 10 from one location to another. The accessory pole receptacles 36 can be configured to removably retain accessory poles, such as, IV poles and/or line management equipment. It should be appreciated that the transport handles 34 can include a curved portion 44 that can be configured to at least partially surround a portion of an accessory pole 40 received in the accessory pole receptacles 36.

The fluid tank receptacle 38 can include a receptacle body 46 with an opening 48 therethrough, a bumper 50, a retainer 52, and a cage 54 as shown in FIGS. 1-10. The opening 50 can be sized to receive a fluid tank 56, such as, for example, an oxygen tank, therein. The retainer 52 can be secured to the receptacle body 46 and can be configured to couple the cage 54 to the receptacle body 46 and movably couple the bumper 50 to the receptacle body 46. The retainer 52 can include a plurality of holes 58 that can be configured to receive a portion of the cage 54 and fasteners used to secure the retainer 52 to the receptacle body 46.

Figure 3:
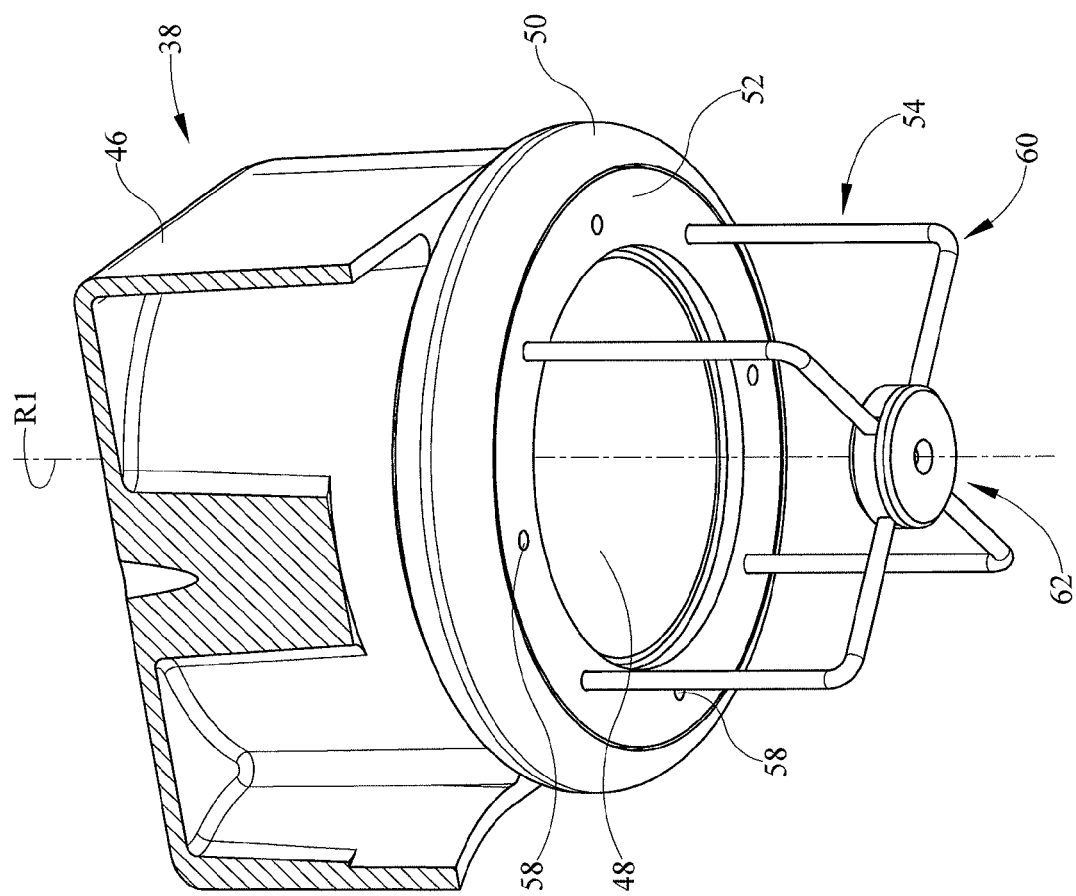
FIG. 3 is a perspective side view of the fluid tank receptacle of FIG. 1.
Figure 4:
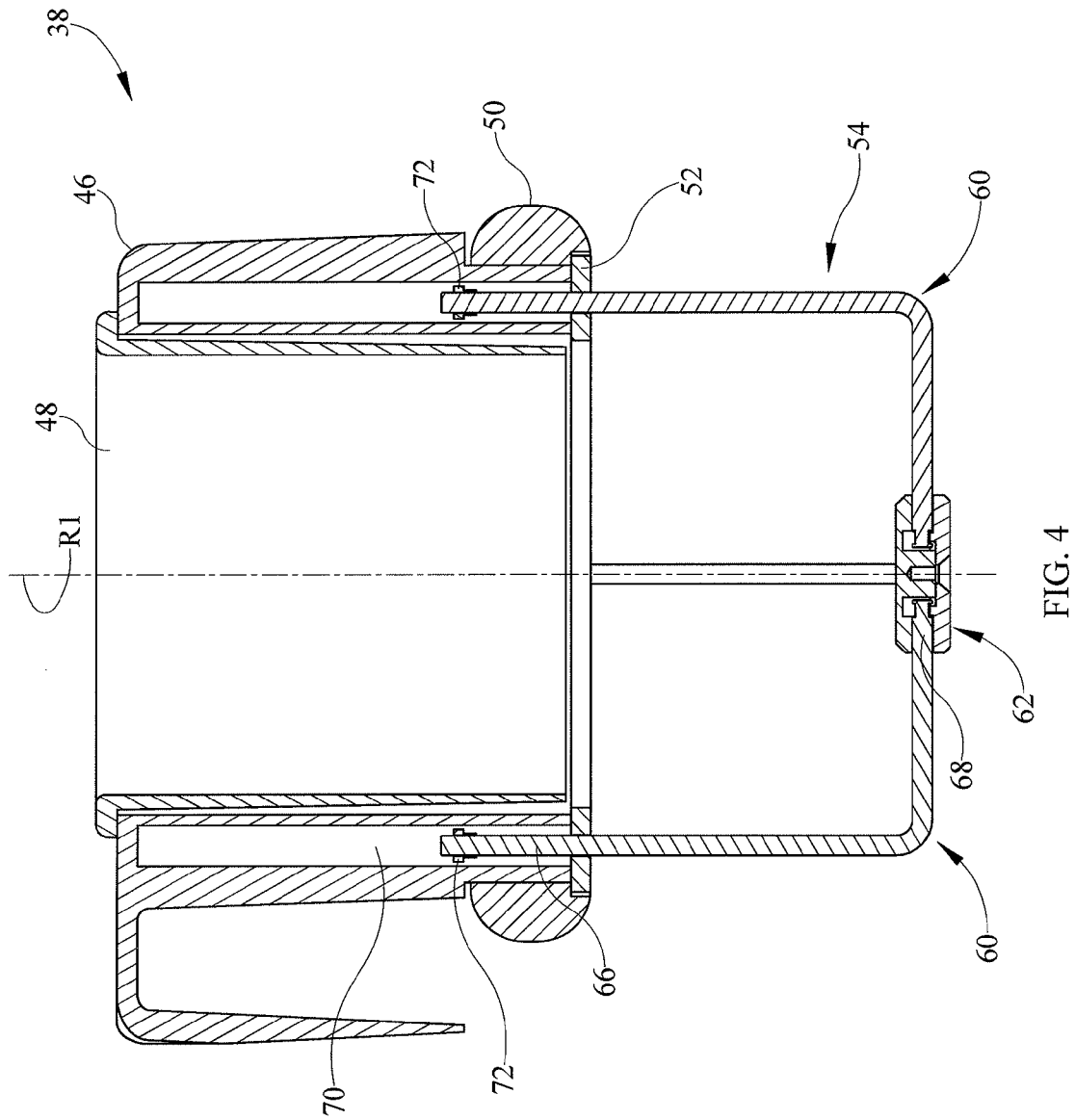
FIG. 4 is a cross-sectional side view of the fluid tank receptacle of FIG. 1 showing the cage in a use position.
Figure 5:
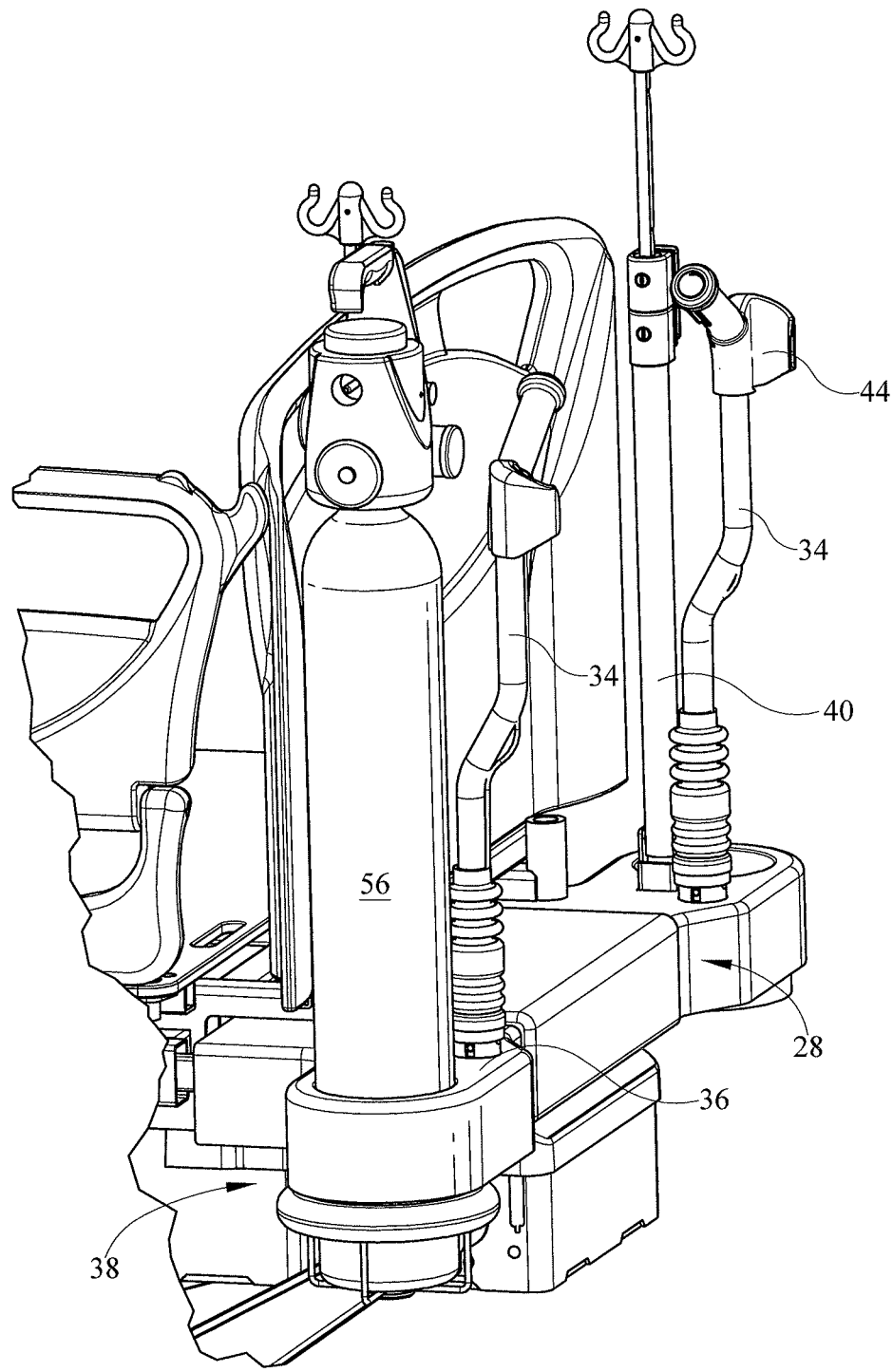
FIG. 5 is a perspective side view of the fluid tank receptacle of FIG. 1 showing a fluid tank received in the fluid tank receptacle.
Figure 6:
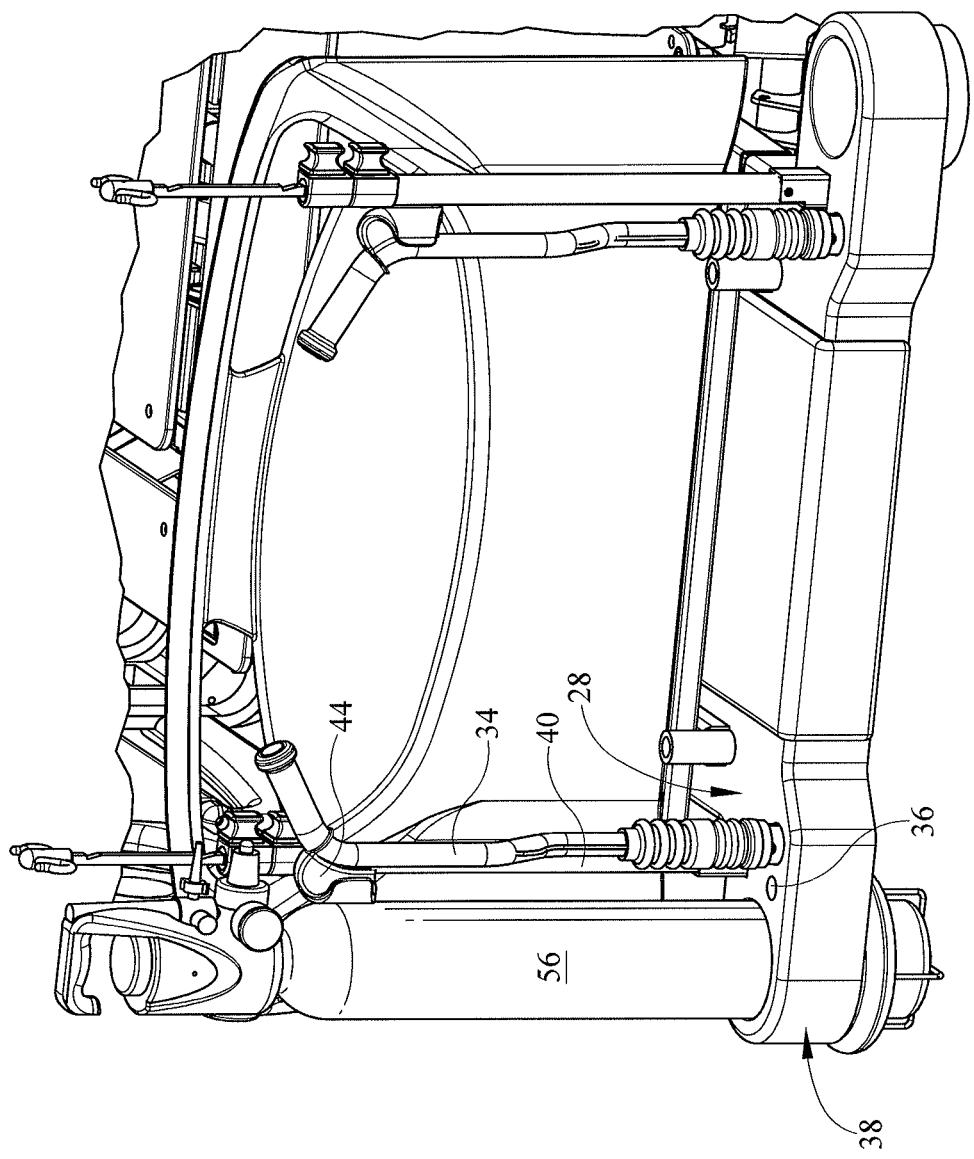
FIG. 6 is a perspective side view of the fluid tank receptacle of FIG. 1 showing the accessory pole receptacle and transport handle.
Figure 7:
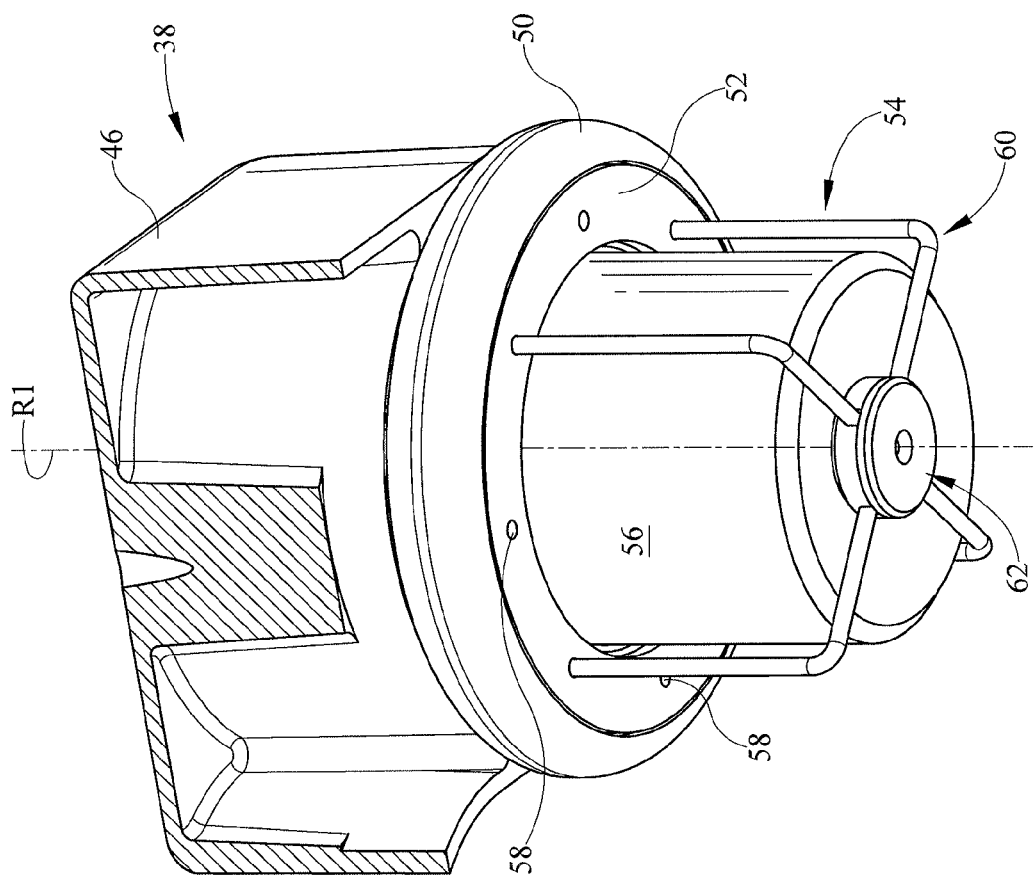
FIG. 7 is a perspective side view of the fluid tank receptacle of FIG. 1 showing the cage in the use position.
Figure 8:
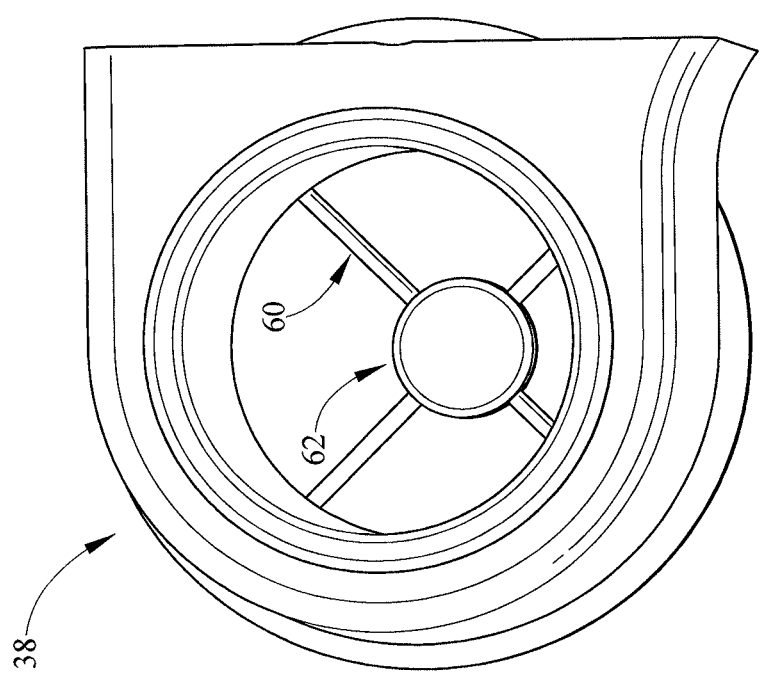
FIG. 8 is a perspective top view of the fluid tank receptacle of FIG. 1.
Figure 9:
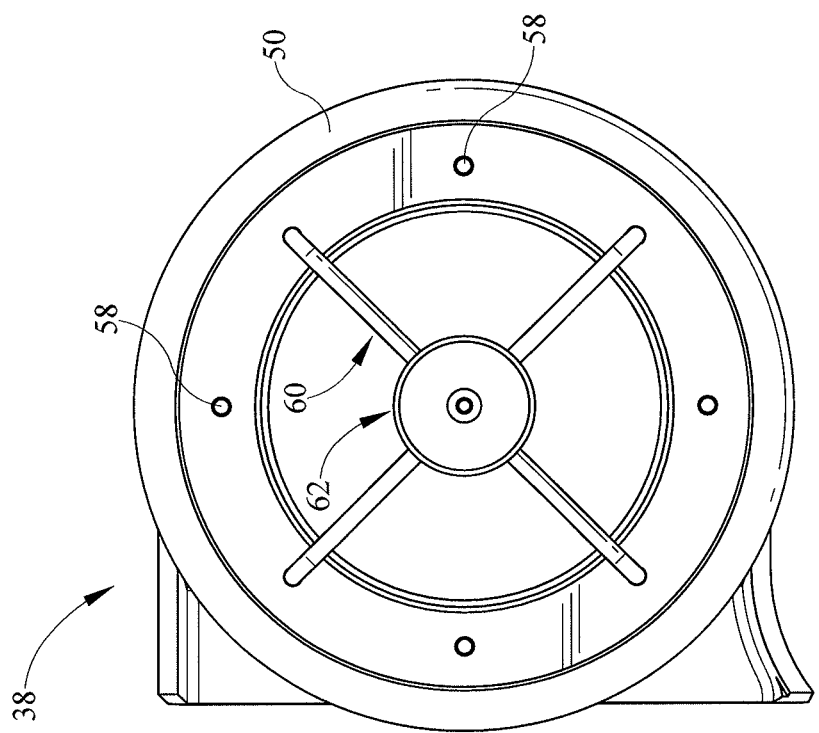
FIG. 9 is a bottom plan view of the fluid tank receptacle of FIG. 1.

The bumper 50 can be configured to absorb some of the force generated when the bumper 50 collides with an object, such as, for example, a wall. In one illustrative embodiment, the bumper 50 can be positioned between the receptacle body 46 and the retainer 52 as shown in FIGS. 3, 4 and 7. The bumper 50 can be configured to rotate about a rotational axis R1 passing through the center of the opening 48. It should be appreciated that the ability of the bumper 50 to rotate can help reduce the force generated when the bumper 50 indirectly collides with an object, such as, a wall.

The cage 54 can be movably coupled to the receptacle body 46 and can be configured to move between a use position where the cage 54 supports a fluid tank 56 received within the fluid tank receptacle 38, and a storage position. The cage 54 can include a plurality of cage supports 60, a support coupler 62, and a plurality of springs 64. The cage supports 60 can include a first support end 66 and a second support end 68. The first support end 66 can be configured to pass through one of the holes 58 in the retainer 52 to slidably engage one of the cage support slots 70 in the receptacle body 46. The second end 68 can be configured to be coupled to the support coupler 62. It should be appreciated that the cage supports 60 can be U-shaped and the second end 68 can pass through another of the holes 58 to engage another of the cage support slots 70. The first support end 66 can include a retaining ring 72 coupled thereto and configured to cooperate with the spring 64 and/or the retainer 52 to maintain the first support end 66 within the cage support slot 70.

The spring 64 can be located in the cage support slot 70 and can be configured to bias the cage 54 toward the storage position. The spring 64 can be positioned between the retaining ring 72 and the retainer 52 as shown in FIG. 10. The spring 64 can be a first length when the cage 54 is in the storage position as shown in FIG. 10 and can be compressed to a second length when a fluid tank 56 engages the cage 54 and moves the cage 54 to the use position. It should be appreciated that the weight of the fluid tank 56 can cause the spring 64 to compress. When the fluid tank 56 is removed, the spring 64 can bias the cage 54 toward the storage position.

The deck 22 can include a head portion 74, a seat portion 76, and a foot portion 78 as shown in FIG. 11. The head portion 74, the seat portion 76, and the foot portion 78 can be movably coupled with each other and/or the upper frame base 20 and can be configured to cooperate with one another to move the deck 22 between a relatively horizontal position and a chair position as shown in FIG. 2. The seat portion 76 can include first and second outer portions 80 and 82 and first and second inner portions 84 and 86. The first and second inner portions 84 and 86 can be positioned between the first and second outer portions 80 and 82. The first and second inner portions 84 and 86 can be movable with respect to the upper frame base 20. In one illustrative embodiment, the first inner portion 84 can be movably coupled to the second inner portion 84 at a first joint 88 and the second inner portion can be coupled to the foot portion 78 at a second joint 90. The first and second outer portions 80 and 82 can be stationary with respect to the upper frame base 20. It should be appreciated that the first and second outer portions 80 and 82 can help reduce incidents of pinch points and maintain the spacing between the deck 22 and the siderails 24 as the first and second inner portions 84 and 86 move with respect to the upper frame base 20.

Many other embodiments of the present disclosure are also envisioned. For example, a person-support apparatus comprises a lower frame, an upper frame, and a deck. The upper frame is movably supported above the lower frame by a support. The deck is supported on the upper frame, the deck includes a section with a first portion configured to be movable with respect to the upper frame and a second portion configured to be stationary with respect to the upper frame. The person-support apparatus is configured to be movable between a generally horizontal position and a chair position.

In another example, a fluid tank receptacle comprises a housing, a cage, and a retainer. The housing includes an opening therethrough configured to receive a fluid tank. The cage movably engages the housing and configured to support the fluid tank. The retainer is coupled to the housing and is configured to movably retain a portion of the cage within the housing such that the cage is able to move between a storage position and a use position with respect to the housing.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

The invention claimed is:

1. A fluid tank receptacle for a patient support apparatus, the fluid tank receptacle comprising:
   a housing with an opening therethrough configured to receive a fluid tank; and
   a support movably engaging the housing and configured to support the fluid tank, a portion of the support being retained within the housing such that the support is able to move between a storage position and a use position with respect to the housing, wherein the support is biased upwardly with respect to the housing and wherein weight of the fluid tank bearing on the support overcomes the bias and translates the support from the storage position to the use position.

2. The fluid tank receptacle of claim 1, wherein the support comprises a cage.

3. The fluid tank receptacle of claim 2, wherein the cage comprises a circular hub and a plurality of cage segments extending from the hub.

4. The fluid tank receptacle of claim 3, wherein each of the cage segments is generally L-shaped.

5. The fluid tank receptacle of claim 4, wherein each cage segment includes a first portion extending radially outwardly from the circular hub and a second portion that is generally perpendicular to the first portion.

6. The fluid tank receptacle of claim 5, further comprising a plurality of springs, each spring being coupled to the second portion of a respective cage segment.

7. The fluid tank receptacle of claim 6, wherein the plurality of springs are located within an interior region of the housing.

8. The fluid tank receptacle of claim 6, wherein movement of the cage downwardly relative to the housing from the storage position to the use position compresses the springs.

9. The fluid tank receptacle of claim 1, further comprising a bumper coupled to the housing.

10. The fluid tank receptacle of claim 9, wherein the bumper is configured to rotate about a rotational axis passing through a center of the opening in the housing.

11. The fluid tank receptacle of claim 9, wherein the bumper is annular in shape and surrounds a lower end portion of the housing.

12. The fluid tank receptacle of claim 11, wherein a portion of the support extends through a bore of the bumper.

13. The fluid tank receptacle of claim 12, wherein the housing has a generally cylindrical inner wall that defines the opening and wherein the portion of the support that extends through the bore of the bumper is situated between the bumper and the generally cylindrical inner wall.

14. The fluid tank receptacle of claim 1, further comprising at least one spring configured to engage the housing and the support to bias the support toward the storage position.

15. The fluid tank receptacle of claim 1, wherein the housing is configured to maintain the fluid tank in a substantially vertical orientation.

16. The fluid tank receptacle of claim 1, wherein the housing has a slot and a portion of the support is received in the slot.

\* \* \* \* \*